US00PP31390P2

(12) United States Plant Patent
O'Connell

(10) Patent No.: US PP31,390 P2
(45) Date of Patent: Jan. 21, 2020

(54) ***SEDEVERIA* PLANT NAMED 'BLUE SPRITE'**

(50) Latin Name: ***Sedeveria* hybrid**
Varietal Denomination: Blue Sprite

(71) Applicant: Altman Specialty Plants, Inc, Vista, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 16/350,544

(22) Filed: Nov. 30, 2018

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP29,643 P3 * 9/2018 O'Connell ..... A01H 5/12
Plt./373

* cited by examiner

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Sedeveria* cultivar named 'Blue Sprite' is disclosed, characterized by a compact concentric, chunky rosette, and unique stem bifurcation which can fill a 9 cm pot with a single vegetative cutting. Thickened blue-green leaves, with enhanced apical rose red blushing. Suitability for combining with other ornamental plants. The new variety would typically be useful as container a plant or as landscape plants.

1 Drawing Sheet

Latin name of the genus and species: *Sedeveria* hybrid.
Variety denomination: 'BLUE SPRITE'.

BACKGROUND OF THE INVENTION

The new cultivar, *Sedeveria* 'Blue Sprite', is the product of a planned breeding program. The new variety originated from a cross pollination of the proprietary, unpatented, seed parent, *Echeveria* hybrid known as 'BEM 11-27' with the pollen parent, an unpatented, hybrid *Sedum* 'SP 9-12' The cross pollination was made during June 2014, in Vista, Calif., at a commercial greenhouse. The new cultivar 'Blue Sprite' was discovered by the inventor, Renee O'Connell, in August 2015, in Vista, Calif., at a commercial greenhouse.

Asexual reproduction of the new cultivar 'Blue Sprite' was first performed in Vista, Calif., at a commercial greenhouse, by terminal vegetative cuttings in Fall of 2017. *Sedeveria* 'Blue Sprite' has since produced multiple generations and has shown that the unique features of this cultivar are stable and reproduced true to type.

SUMMARY OF THE INVENTION

The cultivar 'Blue Sprite' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BLUE SPRITE'. These characteristics in combination distinguish 'BLUE SPRITE' as a new and distinct *Sedeveria* cultivar:

1. *Sedeveria* 'Blue Sprite' produces compact rosettes of thickened leaves, displaying a very "chunky" appearance, not expressed to this extent commonly by other *Sedeveria, Sedums* or *Echeveria.*
2. *Sedeveria* 'Blue Sprite' displays very thickened blue-green leaves, with enhanced apical rose red blushing, a condition accentuated by bright light, cooler temperatures and drought.
3. *Sedeveria* 'Blue Sprite' exhibits a rather unusual trait of bifurcation of the stem, producing multi-headed clusters, as compared to many other *Echeveria* and *Sedum* and hybrids.

PARENTAL COMPARISON

Plants of the new cultivar 'Blue Sprite' are similar to the seed parent in most horticultural characteristics. However, plants of the new cultivar 'Blue Sprite' differ in the following:

1. *Sedeveria* 'Blue Sprite' exhibits stem bifurcation, whereas the *Echeveria* hybrid 'BEM 11-27' produces offsetting from the base.
2. 'Blue Sprite', due to the stem bifurcation, will form a cluster of 7 inches or more in diameter, whereas *Echeveria* hybrid 'BEM 11-27' forms a cluster that rarely exceeds 5" in diameter.
4. *Sedeveria* 'Blue Sprite' expresses more intense apical blushing of the leaves than does *Echeveria* hybrid 'BEM 11-27'.

Plants of the new cultivar 'Blue Sprite' are similar to the pollen parent, in most horticultural characteristics. However, the new cultivar 'Blue Sprite' differs the following:

1. *Sedeveria* 'Blue Sprite' displays stem bifurcation, whereas *Sedum* 'SP 9-12' produces offsetting laterally from the central rosette.
2. *Sedeveria* 'Blue Sprite' exhibits shorter and thickened leaves as compared to *Sedum* 'SP 9-12', contributing to a more "chunky" appearance to the rosette.

COMMERCIAL COMPARISON

The new cultivar 'Blue Sprite' can be compared to *Sedeveria* 'Blue Elf', unpatented'. Plants of this comparator are similar to plants of the new cultivar 'Blue Sprite' in most horticultural characteristics. However, the new cultivar 'Blue Sprite' differs in the following:

1. Foliage color of 'Blue Sprite' is blue-green with rose blushing, foliage of 'Blue Elf' is light grey-green-blue without significant blushing.
2. Plants of 'Blue Sprite' offset much more freely than plants of 'Blue Elf'.
3. Leaves of *Sedeveria* 'Blue Sprite' are thicker than leaves of 'Blue Elf'.

The new cultivar 'Blue Sprite' can be compared to *Sedeveria* 'Jet Beads, unpatented'. Plants of this comparator are similar to plants of the new cultivar 'Blue Sprite' in most horticultural characteristics. However, the new cultivar 'Blue Sprite' differs in the following:

1. Foliage color of 'Blue Sprite' is blue-green with rose blushing, foliage of 'Jet Beads' is greyed-purple with a green base.
2. Plants of 'Blue Sprite' are more robust, and grow more densely than plants of 'Jet Beads'.
3. Leaves of *Sedeveria* 'Blue Sprite' are thicker than leaves of 'Jet Beads'.

The new cultivar 'Blue Sprite' can be compared to *Sedeveria* x *Echeveria* 'Lilac Mist', U.S. Plant Pat. No. 29,643. Plants of this comparator are similar to plants of the new cultivar 'Blue Sprite' in most horticultural characteristics. However, the new cultivar 'Blue Sprite' differs in the following:

1. Foliage color of 'Blue Sprite' is blue-green with rose blushing, foliage of 'Lilac Mist' is lighter grey-green-blue with lighter lavender blushing.
2. Plants of 'Blue Sprite' offset much more freely than plants of 'Lilac Mist'.
3. Leaves of *Sedeveria* 'Blue Sprite' are thicker than leaves of 'Lilac Mist

BRIEF DESCRIPTION OF THE PHOTOGRAPH

The photograph was taken using conventional techniques and equipment. While the colors in the photograph may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of new *Sedeveria* 'Blue Sprite'. The accompanying photograph illustrates in full color a plant of *Sedeveria* 'Blue Sprite', grown in a greenhouse (approximately 2500-foot candles) in Vista, Calif., in a one-quart pot.

DETAILED BOTANICAL DESCRIPTION

In the following description, color references are made to The Royal Horticultural Society Colour Chart, 2007, except where general terms of ordinary dictionary significance are used. The following observations and measurements describe 'Blue Sprite' plants in a commercial greenhouse in Vista Calif. Temperatures ranged from 34° F. to 90° F. night and day. No artificial light, photoperiodic treatments or chemical treatments were given to the plants. Natural light conditions were approximately 2500-4000-foot candles of light. Measurements and numerical values represent averages of typical plant types.

Botanical classification: *Sedeveria* 'BLUE SPRITE'.

PROPAGATION

Type of propagation typically used: Terminal vegetative cuttings.

Time to initiate roots: About 14 days at approximately 24° C.

Root description: Fibrous.

PLANT

Age of plant described: Approximately 4 months.

Container size of the plant described: 1 quart.

Growth habit: Multi headed plant of dense rosettes.

Height: Approximately 8 to 10 cm.

Plant spread: Approximately 18-20 cm.

Growth rate: Rapid.

Branching characteristics: Basal occurring main branches. Bifurcation of upper stem, forming further branching.

*Length*.—About 4 to 6 cm.

*Width*.—8 to 10 mm.

*Color*.—Near RHS Greyed-Brown 199A. Infrequent streaks near Greyed-Green 198A.

*Texture*.—Glabrous, bumpy.

*Strength*.—Very strong.

FOLIAGE

Leaf:

*Arrangement*.—Rosulate. Very evenly and densely arranged.

*Average length*.—Average range 1.5 cm to 2.0 cm.

*Average width*.—8-10 cm.

*Average depth*.—5 mm.

*Width at base*.—5 mm.

*Shape of blade*.—Spatulate.

*Apex*.—Acute to cuspidate.

*Base*.—Truncate.

*Margin*.—Entire.

*Texture of top surface*.—Slightly glaucous.

*Texture of bottom surface*.—Slightly glaucous.

*Appearance of top surface*.—Matte.

*Appearance of top surface*.—Matte.

*Quantity of leaves per plant*.—Approximately 35 to 50 per rosulate head.

*Color*.—Young foliage upper side: Near RHS Green N138C. Apex Greyed-Purple 187C. Young foliage under side: Near RHS Green N138C. Apex Greyed-Purple 187C. Mature foliage upper side: Near RHS Green 138C. Base near 138D, large apical flush near Greyed-Purple 187A. Mature foliage under side: Near RHS Green 138C. Base near 138D, large apical flush near Greyed-Purple 187A.

*Venation*.—There is no visual appearance of venation.

FLOWER

Not observed to date.

REPRODUCTIVE ORGANS

Not observed to date.

OTHER CHARACTERISTICS

Fruits and seeds: Not observed to date.

Temperature tolerance: Tolerates temperatures from approximately −2° C. to at least 35° C.

Disease/pest resistance: Neither resistance or susceptibility to normal diseases and pests of *Sedeveria* or *Echeveria* has been observed.

Drought tolerance: Tolerates at least 3 weeks of high temperatures without supplemental water, showing no serious damage to plant.

What is claimed is:

1. A new and distinct cultivar of *Sedeveria* plant named 'BLUE SPRITE' as herein illustrated and described.

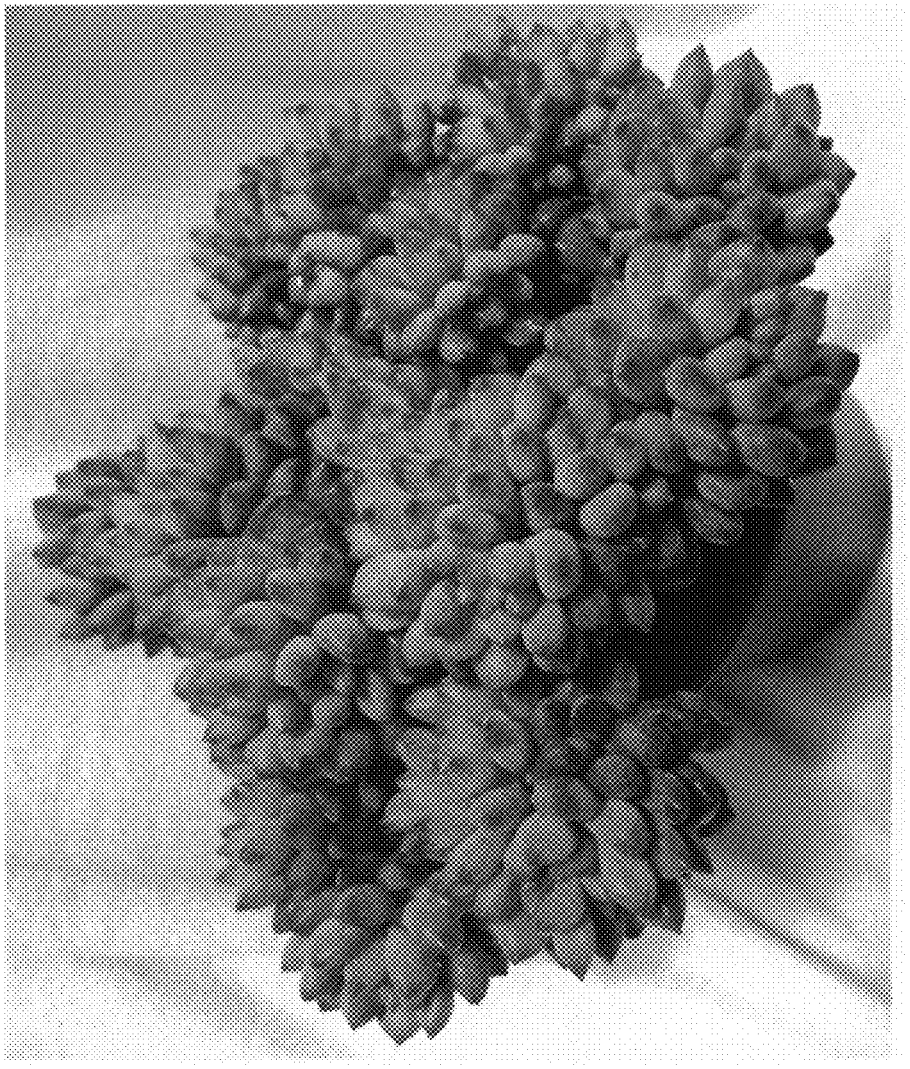

* * * * *